(12) United States Patent
Tellman et al.

(10) Patent No.: US 9,956,599 B2
(45) Date of Patent: May 1, 2018

(54) SYSTEM, INCLUDING A BENDING BAR AND A BENDING CAGE, FOR BENDING A PLATE IN A PLANE OF THE PLATE

(71) Applicant: TriMed, Inc., Valencia, CA (US)

(72) Inventors: Lukas Tellman, Falsterbo (SE); Randall James Sovereign, Santa Clarita, CA (US)

(73) Assignee: TRIMED, INC., Valencia, CA (US)

( * ) Notice: Subject to any disclaimer, the term of this patent is extended or adjusted under 35 U.S.C. 154(b) by 0 days. days.

(21) Appl. No.: 15/278,590

(22) Filed: Sep. 28, 2016

(65) Prior Publication Data

US 2017/0087614 A1 Mar. 30, 2017

Related U.S. Application Data

(60) Provisional application No. 62/234,236, filed on Sep. 29, 2015.

(51) Int. Cl.
| | |
|---|---|
| *B21D 7/02* | (2006.01) |
| *B21D 5/00* | (2006.01) |
| *B21D 11/20* | (2006.01) |

(52) U.S. Cl.
CPC ............... *B21D 7/02* (2013.01); *B21D 5/00* (2013.01); *B21D 11/20* (2013.01)

(58) Field of Classification Search
CPC .... B25B 5/02; B25B 7/02; B25B 7/08; B25B 7/10; B25B 7/12; A61B 17/8861; B21D 7/06; B21D 7/063; B21D 9/08; B21D 9/085
USPC ........................................... 81/302, 486, 3.7
See application file for complete search history.

(56) References Cited

U.S. PATENT DOCUMENTS

| | | | |
|---|---|---|---|
| 638,662 A | 12/1896 | Dow | |
| 801,151 A | 10/1905 | McKeever | |
| 2,409,627 A | 10/1946 | Helgeson | |
| 4,121,486 A * | 10/1978 | Frank | B23G 9/009 15/104.04 |

(Continued)

FOREIGN PATENT DOCUMENTS

| | | |
|---|---|---|
| GB | 417656 | 10/1934 |
| WO | 2014/107144 A1 | 7/2014 |

*Primary Examiner* — Debra Sullivan
(74) *Attorney, Agent, or Firm* — Ladas & Parry LLP

(57) ABSTRACT

A system and method for bending a bone fixation plate in the horizontal plane of the plate. The apparatus and method provide for optimization of applied bending moments by controlling the orientation of a bending tool to prevent deviation from an axis of bending. The system includes a bending bar or bars with an aperture or slot for engaging a plate or rod and a bending cage that can be in the shape of a rectangular box having a front surface separated from a rear surface by a distance. The front surface has a front elongate opening and the rear surface has a rear elongate opening. The front and rear openings are each formed by two parallel edges separated by a vertical distance and having a horizontal length. The relative dimensions of the respective bending bars and openings are such that the bending cage can be used to permit free movement of the bending bars in a direction parallel to the primary axis of the elongate openings but to prevent rotational movement of the bending bars about an axis substantially parallel to the length of the bending bars.

20 Claims, 9 Drawing Sheets

(56) References Cited

U.S. PATENT DOCUMENTS

| | | | | |
|---|---|---|---|---|
| 5,161,404 A | * | 11/1992 | Hayes | B21D 7/063 |
| | | | | 140/106 |
| 5,389,099 A | * | 2/1995 | Hartmeister | A61B 17/8863 |
| | | | | 606/101 |
| 5,564,302 A | * | 10/1996 | Watrous | A61B 17/8863 |
| | | | | 72/458 |
| 5,595,100 A | | 1/1997 | Sollo | |
| 2005/0139043 A1 | | 6/2005 | Kang | |
| 2006/0150699 A1 | | 7/2006 | Garner et al. | |

* cited by examiner

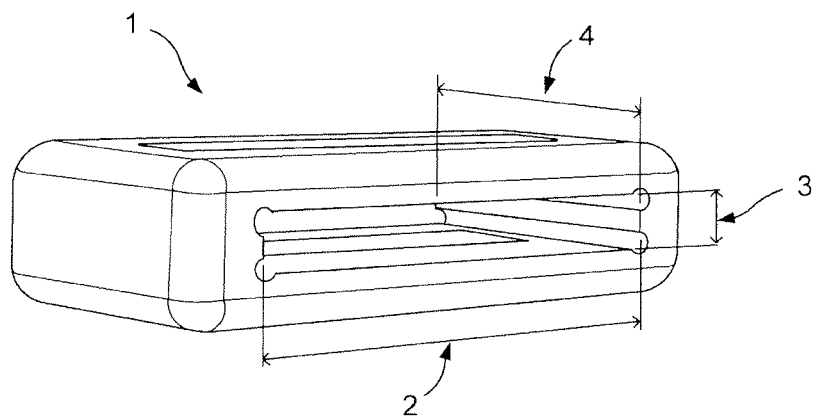
F I G. 11
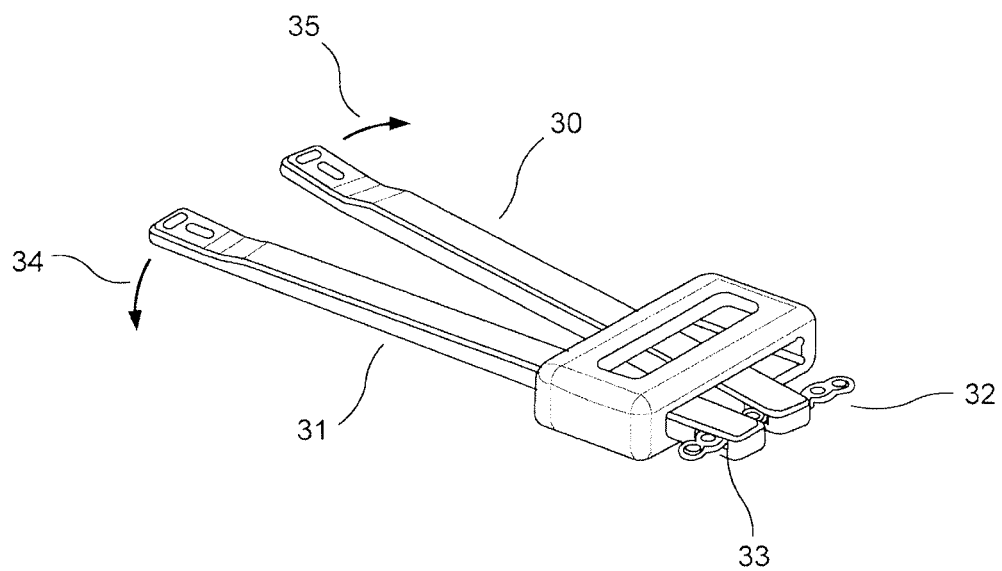
F I G. 12

SYSTEM, INCLUDING A BENDING BAR AND A BENDING CAGE, FOR BENDING A PLATE IN A PLANE OF THE PLATE

CROSS REFERENCE APPLICATION

This application claims the benefit of U.S. Provisional Application Ser. No. 62/234,236 filed Sep. 29, 2015, the content of which is incorporated herein by reference.

FIELD OF THE INVENTION

The present invention relates to an instrument for bending a bone fixation plate in the horizontal plane of the plate. More particularly, the instrument provides for optimization of applied bending moments by controlling the orientation of a bending tool to prevent deviation from an axis of bending.

BACKGROUND OF THE INVENTION

Plate and screw fixation of bones is a generally accepted method of treatment for several types of conditions that affect structural integrity of skeletal elements. A majority of plates are made from a malleable material such as a metal or metal alloy. One advantage of these types of materials is that they allow modification of the shape of the plate for more intimate contact with a bone surface which often may have a complex surface topography. Because of this need, it may often be required to bend bone plates along any of the three principle axes in order to provide a plate contour that more closely matches the surface anatomy at the site of application.

The majority of instruments used to bend or modify the shape of bone plates use some form of leverage to allow amplification of an applied manual force to cause bending of the typically much stronger metal plate. A basic bending tool is often a pair of flat bars of a given length. The flat bars at their ends capture a portion of a bone plate through an aperture or slot (see, for example, FIG. 1.). This type of tool, sometimes called a bending iron, is simple, requires relatively little space, and often is easily adapted to fit inside the utilized instrument or implant tray. This type of tool also has the advantage that it is light and simple for a user to manipulate. Bending irons are most effective for creating a vertical bend in a plate or producing a bend around an axis transverse to the long axis of the plate (see, for example, FIG. 1). This bending axis is resisted only by the thickness of the plate which is the plate's smallest dimension and therefore is the bending direction that requires the least amount of bending force.

The opening in the bending iron is a larger size than the dimensions of the plate itself in order to simplify insertion of the plate into the opening of the bending tool. As a result, this introduces some slop and rotational play between the opening and the implant. Fortunately, when a bending iron is used to bend a plate vertically around an axis transverse to the long axis of the plate, the plate seeks its most stable position in the opening of the instrument as the bending force is applied. This position of stability naturally aligns the bending instrument into a single, congruent plane and allows the applied force to be efficiently and completely transferred along this desired axis of bending. For this reason, these types of instruments work fairly well for creating plate bends in a vertical direction.

A bending iron is also generally effective for creating torsional bends around the long axis of a plate. Again, when used in this manner, as the torsional bending force is applied to the bending iron, the plate will twist within the opening of the slot or aperture until contact occurs along opposite diagonal edges of the plate in the opening. This natural position of stability again maintains the two bending tools along parallel but offset planes, allowing the application of force to be effectively and completely transferred to the plate around the desired torsional axis of bending. Although adding a torsional bend requires more force than applying a simple vertical bend as described previously, this feature can be overcome by providing a bending iron of sufficient length to gain the requisite mechanical advantage.

Unfortunately, plates sometime require the addition of a horizontal bend, around an axis that is perpendicular to the plane of the plate. In this direction of bending, bending irons typically do not work well, if at all. Because the slot or opening in the bending iron is oversized relative to the plate dimensions to allow easy insertion of the plate into the bending iron as well as accommodate other bends or contours of the plate, as bending force is applied to create a horizontal bend, the bending irons rotate around the axis of the plate to find the position of maximal stability. This causes the bending tools to stabilize in a position that is not opposite and coplanar, resulting in misdirection of the applied bending force in a direction that is outside the plane of the plate. This discrepancy in the direction of applied bending force and the desired direction of plate bending either creates a bending in a direction that is undesired or more commonly can prevent a bend from being created at all because bending is effectively applied over a larger dimension.

In addition, the torsional play of the plate within the opening of the bending tool results in a tendency for the end of the plate to slip out of the bending tool. Since this direction of bending is typically the most difficult, being through the width of the plate rather than the thickness, any torsional movement of the plate (1) reduces the effectiveness of maintaining all of the applied load along the desired axis of the bend, and (2) directs a bending axis that is oblique to any principle axis of the plate resulting in significant increase in the amount of applied load required to create a plate bend. Often, this may exceed the ability of a user to generate the required force.

Other bending instruments have been used, but require much heavier, bulkier, and more costly types of instruments. See, for example, FIGS. 2, 3, and 4 which show existing bending instruments that are currently in use (in addition to the instrument of FIG. 1). These instruments still have the problematic issue of controlling a bending force to be efficiently and effectively transferred to the plate in a horizontal direction (around the axis that is perpendicular to the plane of the plate). In addition, these instruments do not address the tendency for the plate to twist or slip out of the holding bracket while this type of force is applied.

SUMMARY OF THE INVENTION

In accordance with a first embodiment of the invention, there is provided a system for bending a plate or rod, comprising
   (a) at least a first elongate bending bar comprising first and second ends and a body portion between the first and second ends, the first elongate bending bar having a longitudinal axis, the body portion comprising an upper surface and a lower surface defining a thickness t, the first end comprising an aperture or slot for engaging the plate or rod such that, with the plate or rod engaged in the aperture or slot, a bending force can be applied to the plate or rod by application of force to the second end of the first elongate bending bar; and (b) a bending cage comprising a hollow interior and opposed front and rear surfaces separated by a distance d, each of the opposed front and rear surfaces defining an elongate opening formed with respective upper and lower parallel edges, each of the respective openings having a primary axis along a length thereof, respective dimensions of the respective openings, the distance d and the first elongate bending bar being such that (i) the first elongate bending bar is insertable through one of the respective openings in the front or rear surface to an operable position wherein the body portion of the first elongate bending bar is disposed within the bending cage with the first and second ends of the first elongate bending bar disposed outside of the bending cage at opposing sides of the bending cage, and (ii) with the first elongate bending bar in said operable position, the respective upper and lower parallel edges of the openings are disposed with respect to the upper and lower surfaces of the first bending bar so as to permit lateral movement of the first bending bar in a direction parallel to the primary axes of the respective openings but to restrict rotational movement of the bending bar about an axis substantially parallel to the longitudinal axis of the bending bar whereby, with the first bending bar in the operable position in the bending cage and the plate or rod engaged in the aperture or slot in the first end of the first bending bar, the bending cage restricts transfer of bending forces applied to the plate or rod by application of force to the second end of the first bending bar to an axis that is parallel to the primary axes of the respective openings.

The respective elongate openings in the front and rear surfaces of the bending cage may be of the same dimensions. Preferably, the bending cage is of rectangular shape and has, in addition to the front and rear surfaces, side walls, a bottom and a top. The bottom, the top or both of the bending cage may comprise an opening therein to reduce the weight and bulk of the bending cage.

In a second embodiment of the invention, there is provided a system for bending a plate or rod, comprising (a) at least first and second elongate bending bars each comprising first and second ends and a body portion between the first and second ends, each of the first and second bending bars having a longitudinal axis, the body portion of each of the first and second bending bars comprising an upper surface and a lower surface defining a thickness t, the first end of each of the first and second bending bars comprising an aperture or slot for engaging the plate or rod such that, with the plate or rod engaged in the apertures or slots of the respective first and second bending bars, a bending force can be applied to the plate or rod by application of force to the second ends of the respective bending bars; and (b) a bending cage comprising a hollow interior and opposed front and rear surfaces separated by a distance d, each of the opposed front and rear surfaces defining an elongate opening formed with respective upper and lower parallel edges, each of the respective openings having a primary axis along a length thereof with the respective primary axes of the respective openings being parallel to one another, respective dimensions of the respective openings, the distance d and the first and second bending bars being such that (i) the first and second bending bars are insertable through one of the respective openings in the front or rear surface to an operable position wherein the respective body portions of the first and second bending bars are disposed within the bending cage with the respective first and second ends of the first and second bending bars disposed outside of the bending cage at opposing sides of the bending cage, and (ii) with the first and second bending bars in said operable position, the respective upper and lower parallel edges of the openings are disposed with respect to the respective upper and lower surfaces of the first and second bending bars so as freely to permit lateral movement of the first and second bending bars in a direction parallel to the primary axes of the respective openings but to restrict rotational movement of the first and second bending bars about an axis substantially parallel to the respective longitudinal axes of the first and second bending bars whereby, with the first and second bending bars in the operable position in the bending cage and the plate or rod engaged in the apertures or slots in the respective first ends of the first and second bending bars, the bending cage restricts transfer of bending forces applied to the plate or rod by application of force to the respective second ends of the first and second bending bars to an axis that is parallel to the primary axes of the respective openings.

The respective lengths of the elongate openings of the first and second bending bars may be such that, with the first and second bending bars in the operable position, with the plate or rod engaged in the respective apertures or slots of the respective first ends of the first and second bending bars and with the respective first ends of the first and second bending bars adjacent to each other, the first and second bending bars can be moved in the direction parallel to the respective primary axes of the respective elongate openings a distance sufficient to increase an angle between the first and second bending bars from 0° to 45°.

In accordance with yet another embodiment of the invention, there is provided a method for bending a plate or rod sideways in a plane of the plate or rod, the method comprising:

(a) providing the system comprising the first and second bending bars;

(b) inserting the first and second bending bars through the respective elongate openings in the front and rear surfaces of the bending cage;

(c) inserting the plate or rod in the respective apertures or slots at the respective first ends of the first and second bending bars; and (d) applying force to the respective second ends of the first and second bend bars to move the respective second ends of the first and second bending bars apart or further apart whereby to impart a bending force on the plate or rod in the plane of the plate or rod.

In accordance with a still further embodiment of the invention, there is provided a system for bending an implant in a single plane, said system comprising (a) at least a first elongate bending bar having a first end, a second end, and a body disposed between the two, said first end having at least one of an aperture or slot for engaging the outer surface of at least a portion of said implant at a point of contact;

(b) a bending cage comprising at least one of an aperture or slot for allowing insertion of said bending iron into the bending cage, and means for (i) allowing the bending iron inserted into the bending cage movement along a single plane while constraining translational movement and rotation of the bending iron out of said plane, and (ii) engaging said bending iron at a site of contact such that distraction of said second end of the bending iron in relation to said bending cage results in creation of a torque to bend said implant around an axis that is located adjacent to the point of contact of said first end of the bending iron with said implant.

In each of the preferred embodiments, a thickness of the elongate bending bar(s) is nominally smaller or only slightly larger than the vertical distance of the openings in the front and rear surfaces of the bending cage so as to permit free movement of the elongate bending bar(s) in a direction parallel to a primary (horizontal) axis of the front and rear openings of the bending cage, but to prevent a rotational movement of the elongated bending bar(s) about an axis parallel to their length. In other words, the bending cage allows free motion of the elongate bending bar(s) along a primary, horizontal axis in the elongate openings of the front and rear surfaces of the bending cage while restricting clockwise and counterclockwise rotational movements of the bending bar(s) along other axes.

BRIEF DESCRIPTION OF THE DRAWINGS

The features and advantages of the present invention will be more readily understood from a detailed description of the exemplary embodiments taken in conjunction with the following figures.

FIG. 11 shows another perspective view of the bending cage of the present invention in a preferred embodiment.

FIG. 12 shows a further perspective view of the bending cage with bending irons inserted therein according to a preferred embodiment of the present invention.

The invention will next be described in connection with certain exemplary embodiments. However, it should be clear to those skilled in the art that various modifications, additions, and subtractions can be made without departing from the spirit or scope of the claims.

DETAILED DESCRIPTION OF THE INVENTION

Figure 1:
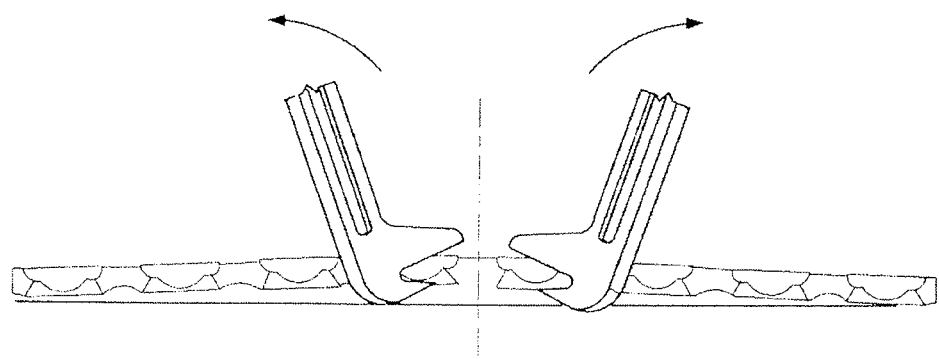
FIG. 1 shows a traditional bending bar or iron for bending a bone fixation plate. This typical bending tool has a slot at the end of the instrument for inserting the plate and is used for bending the plate along an axis that is transverse to the long axis of the plate.
Figure 2:
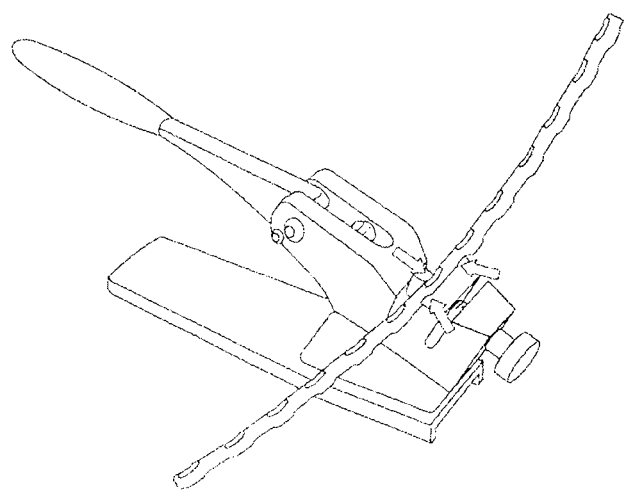
FIG. 2 shows an example of a table type bending vise. This clamp type bending tool is heavy and bulky, and usually impossible to fit in an implant or instrument tray.
Figure 3:
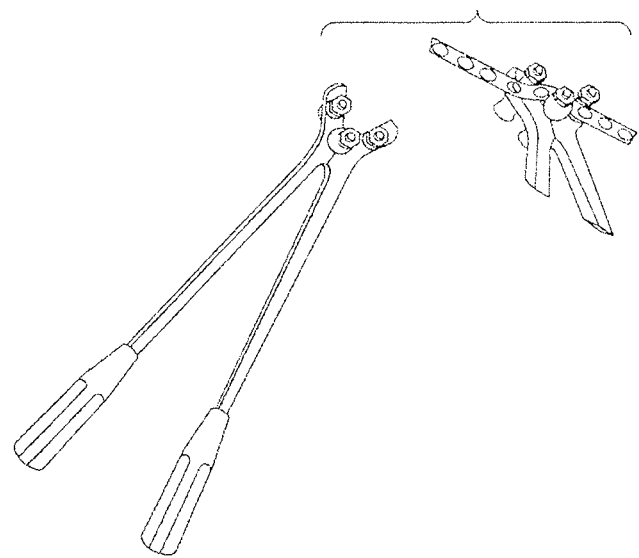
FIG. 3 shows a pliers-type bending tool which uses three-point bending around a rotational axis. If this tool is used for horizontal bending, it is difficult to keep the plate from twisting without a track dedicated to a particular plate geometry. This type of bending tool is also bulky.
Figure 4:
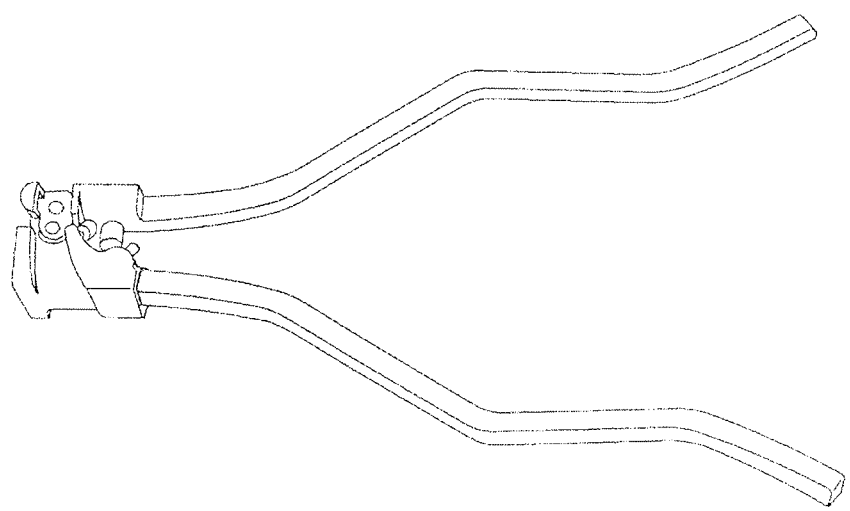
FIG. 4 shows another example of a pliers-type bending tool.
Figure 5:
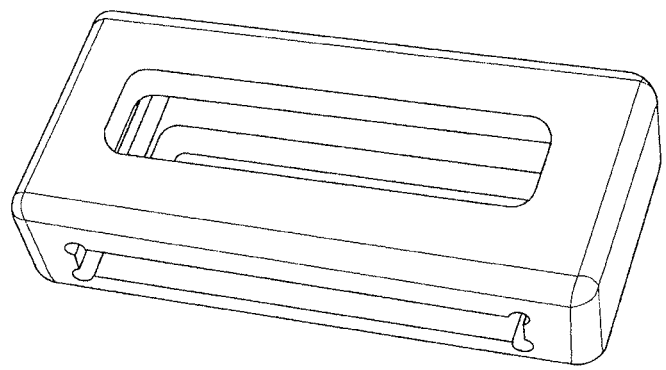
FIG. 5 shows a perspective view of a bending cage according to the present invention in a preferred embodiment.
Figure 6:
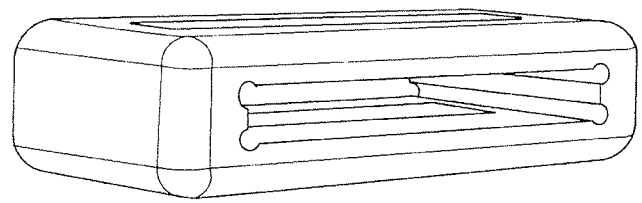
FIG. 6 shows another perspective view of the bending cage of the present invention in a preferred embodiment.
Figure 7:
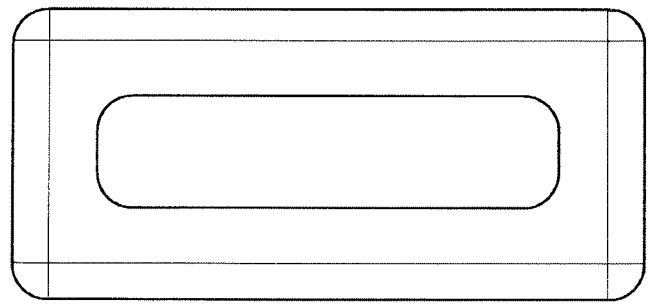
FIG. 7 shows a top view of the bending cage of the present invention in a preferred embodiment, the bottom view being the same.
Figure 8:
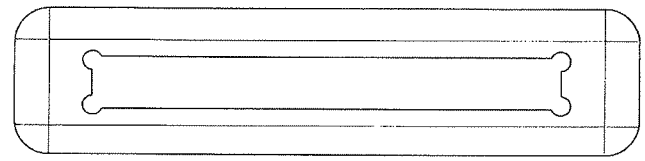
FIG. 8 shows a front view of the bending cage of the present invention in a preferred embodiment, the rear view being the same.
Figure 9:
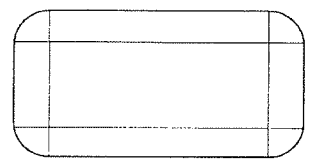
FIG. 9 shows a right side view of the bending cage of the present invention in a preferred embodiment, the left side view being the same.
Figure 10:
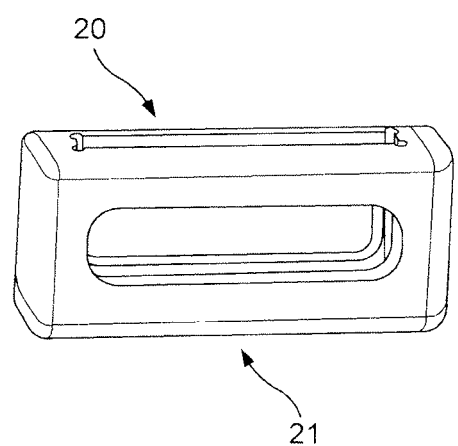
FIG. 10 shows a top perspective view of the bending cage of the present invention in a preferred embodiment.

As shown in FIG. 10, in a preferred embodiment, the bending cage (1) has a front opening (20) and a rear opening (21), each dimensioned to allow passage of a bending bar or bending iron (30, 31).

FIG. 11 shows the front opening (20) of the bending cage (1) having two parallel edges separated by a vertical distance (3) and having a horizontal length (2). The vertical distance (3) allows a snug fit for a vertical dimension (e.g., thickness) of a bending bar or bending iron (30, 31) while the horizontal length (2) permits free horizontal motion for the bending bar or being iron (30, 31) within the front opening (20). Thus, a range along horizontal length (2) is provided for moving at least one bending iron (30, 31) in a horizontal direction while vertical distance (3) prevents spinning or rotational movement of the bending bar or bending iron (30, 31) and maintains an applied force constrained along an axis directed by the horizontal length (2) in the bending cage (1).

The bending cage (1) has a rear opening (21) that is separated from the front surface (20) by distance (4). The front and rear openings (20, 21) provide a plane of support to the surface of the bending irons (30, 31) by providing two separate parallel and aligned constraints separated by a distance (4). The separation provided by distance (4) of the openings (20, 21) provides further torsional constraints to the bending irons (30, 31) that are passed through the bending cage (1).

Figure 13:
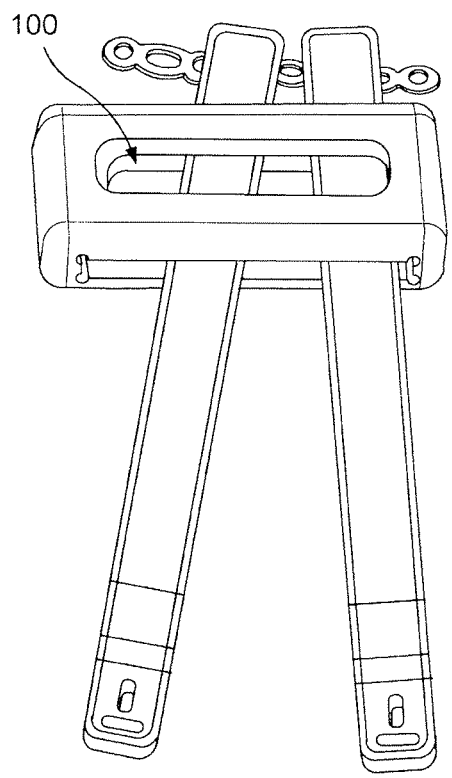
FIG. 13 shows yet another perspective view of the bending cage with bending irons inserted therein according to a preferred embodiment of the present invention.

In an embodiment shown in FIG. 13, an empty space (100) is cut out of the top and bottom surfaces of the bending cage (1) to further reduce the weight and bulk of the bending cage (1). In other embodiments not shown, the top and bottom surfaces of the bending cage (1) are solid and no empty space (100) is cut out of the top and bottom surfaces of the bending cage (1).

Figure 14:
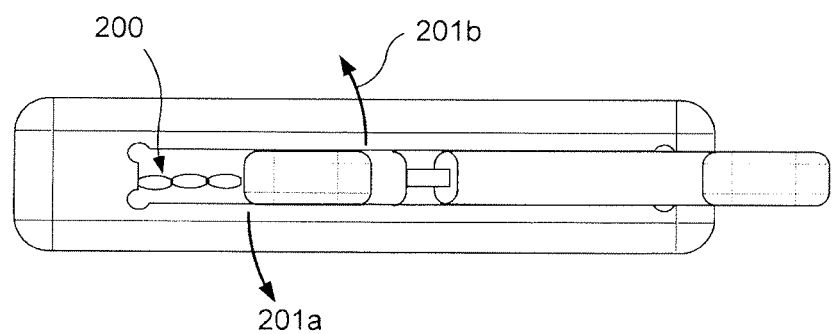
FIG. 14 shows a front view of the bending cage with bending irons inserted therein according to a preferred embodiment of the present invention.

One preferred embodiment of the present invention includes a combination of bending bars or bending irons (30, 31) and a bending cage (1). FIGS. 12, 13, and 14 show a combination of the bending cage (1) and first (30) and second (31) bending bars or irons for bending a bone plate (32) horizontally along an axis that is perpendicular to the plane of the plate (32). The bone plate (32) is captured by an aperture or slot (33) in the first bending iron (31) and by a similar aperture or slot in the second bending iron (30).

As shown in FIG. 12, in order to bend the bone plate (32), a user applies opposing forces (34) and (35) to the distal ends of the bending irons (30, 31) opposite the side of the opening or slot (33) to impart an angular bending force to the bone plate (32) around an axis that is parallel to an axis perpendicular to the plane of the plate (32).

The front opening (20) of the bending cage (1) is constructed with an upper surface and lower surface that are parallel and separated by a dimension (3) that is slightly larger than the thickness of bending irons (30, 31). As shown in FIG. 14, this allows free motion along a primary axis (200) while restricting counterclockwise rotational movement of the bending irons (30, 31) according to arrows (201a) and (201b) shown in FIG. 14 or clockwise rotational motion in an opposite direction. In this way, the bending cage (1) simply and effectively limits bending forces to opposite, but coplanar bending loads in the plane of the plate.

In a preferred embodiment of the invention, the bending bar or bars are flat with a length of 10 to 50 cm, and more preferably 15 to 40 cm; a width of 0.5 to 4 cm and more preferably 1 to 3 cm; and a thickness t of 0.5 to 4 cm, more preferably 1 to 3 cm.

In a preferred embodiment, the opening in the bending cage can be slightly bigger than, the same size as or slightly smaller than the bending irons. For example, a difference between the thickness t of the bending iron or irons and the distance between the upper and lower edges of the opening in the front surface of the bending cage can range from about +350 um to −350 um where a negative number would represent a friction fit and a positive number would provide some play. In a preferred embodiment the opening is slightly smaller than the bending irons to purposefully friction fit the bending irons into the bending cage so that it doesn't easily come apart by mistake.

In a preferred embodiment, the distance 4 is about 2 to 10 cm, more preferably 3 to 7 cm in length. The front and rear surfaces preferably have a length of 5 to 25 cm, more preferably about 8 to 18 cm; and preferably have a width of 2 to 10 cm, more preferably about 2 to 8 cm. The elongate opening in each of the front and rear surfaced of the bending cage is preferably between about 4 and 22 cm in length, more preferably about 6 to 20 cm.

In another preferred embodiment, wherein the system comprises first and second bending bars, which can be moved in the direction parallel to the respective primary axes of the respective elongate openings a distance sufficient to increase the angle 36 (FIG. 12) between the first and second bending bars from 0° to 45°.

In yet another preferred embodiment, the bending cage is rectangular with a hollow interior to permit the bending bar or bars to pass through the opening in the front surface, through the bending cage and out the opening in the rear surface. The provision of a hollow interior also decreases the weight of the bending cage, which preferably will be within a range of 0.1 to 0.9 lbs. In this connection, the bending cage will be made of a material that is strong enough to provide for the bending function described herein but light enough that it can be easily handled. Preferred materials for the bending cage are plastics such as plastic polymers or fiber reinforced compounds.

From the above, it may be appreciated that the systems and methods of the invention can be designed so as to allow bending to occur in a way that each bending iron (or bending bar) rotates through the center of attachment where that bar grabs the plate; thus each bar can rotate on its own center at the far end. This means that the site of connection of each bar with the plate doesn't slide along the surface of the plate during the bend. This eliminates frictional forces which retard or prevent the bend from occurring, as well as reduces damage to the surface skin of the plate as it is being bent.

Furthermore, since the applied forces to bend a plate in the plane of the plate create a rotational component of torque along the axis of each bending iron (which can add an undesired twisting bend to the plate), the cage independently prevents any such rotation of the bending irons from occurring while the bending moment is applied.

Moreover, so long as there is no direct connection between the first bending iron and the rest of the device, there is provided free and un-fettered translational motion between the bending iron and the rest of the system. At the same time, all rotational movement along the axis of the bending iron is prevented. This combination makes the device simple to apply, simple to use, and simple to remove.

So, in summary, in a preferred system according to the invention, there can be provided a number of basic features:
1. The two bending irons have no direct connection to each other.
2. Each bending iron has unrestricted movement along the plane of the bend.
3. Each bending iron is prevented from rotating along an axis out of the plane of the bend.
4. There is no translation of either bending iron during application of the bend at the site of capture of the bending iron and the plate itself.

Figure 15:
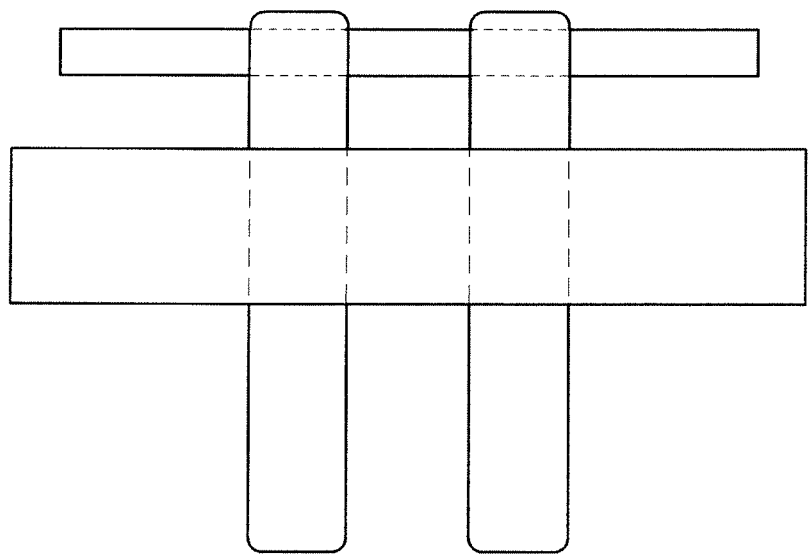
FIG. 15 shows a system according to the invention comprising two bending irons inserted in a bending cage with the bending irons engaging a plate and being disposed in an initial position.

FIGS. 15-19 show the advantages of having the bending irons rotate around the point where they capture the plate being bent. FIG. 15 shows the initial position before bending.

Figure 16:
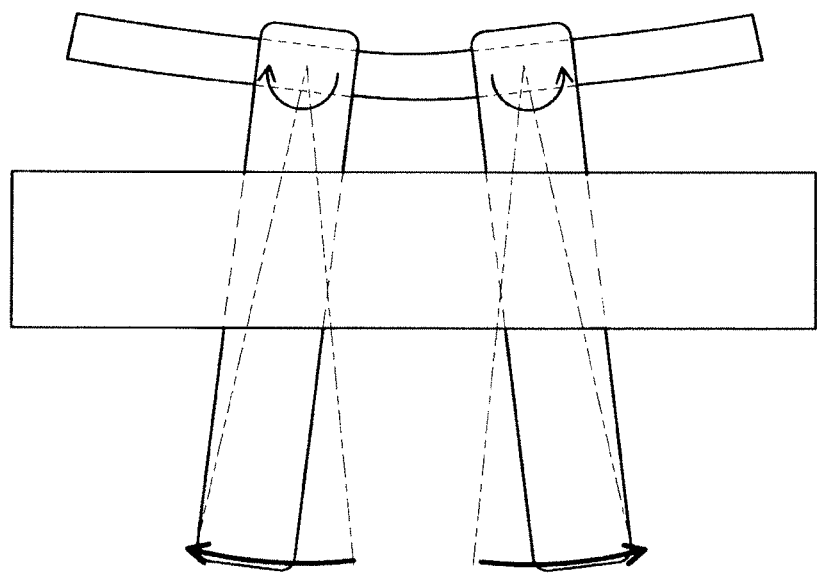
FIG. 16 shows the system of FIG. 15 with the bending irons moved to a second position to bend the plate.
Figure 17:
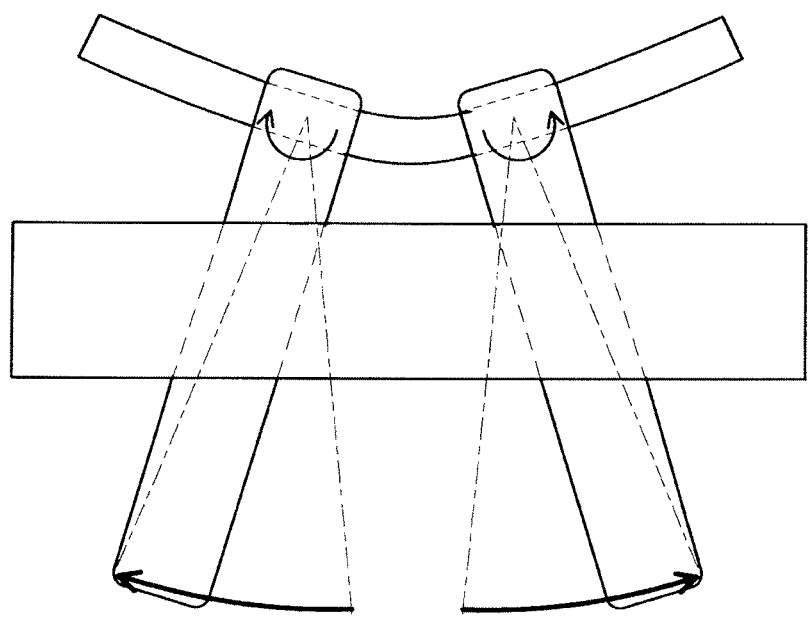
FIG. 17 shows the system of FIG. 15 with the bending irons moved to a third position to bend the plate.
Figure 18:
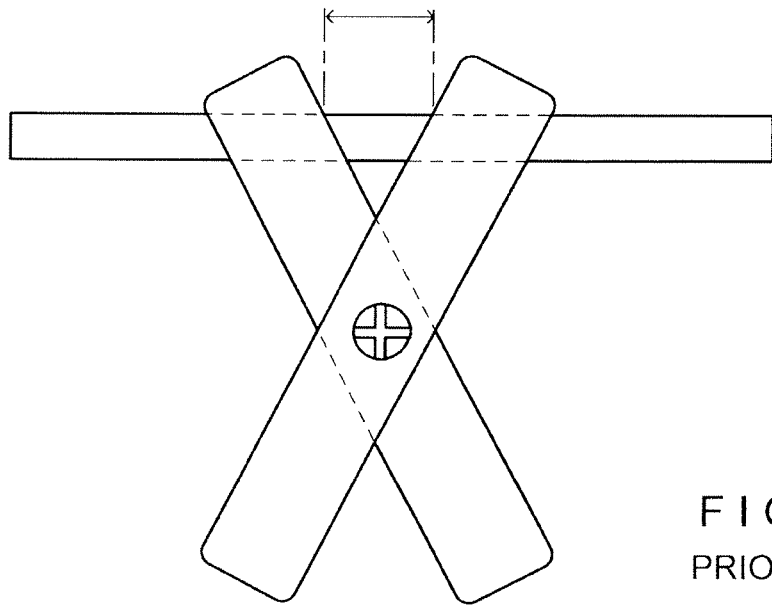
FIG. 18 shows a pliers type bending apparatus of the prior art engaging a plate with the respective arms of the pliers in an initial position.
Figure 19:
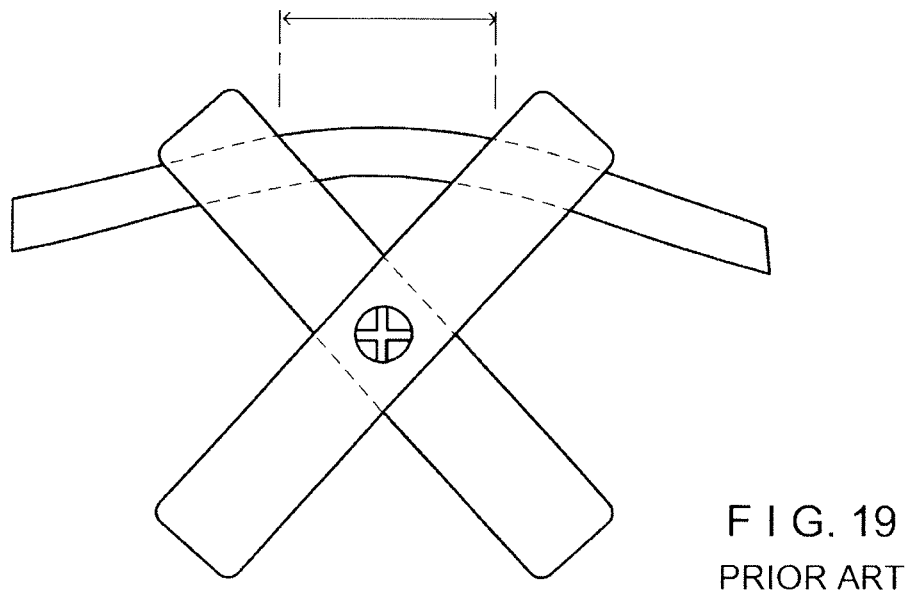
FIG. 19 shows the pliers type bending apparatus of FIG. 18 with the respective arms of the pliers in a second position bending the plate.

FIGS. 16 and 17 show how the pivot point of each bending iron is at the site of engagement with the plate. This allows bending of the plate without causing the bending iron to scrape along the surface of the plate as with a design that uses a pin or pivot point to join the two arms of the instrument together. To show the contrast, FIGS. 18 and 19 demonstrate that a 'pliers' type of apparatus causes a change in length of the plate to occur. This means at least one arm of the apparatus has to scrape along the surface of the plate.

Although a preferred system of the invention comprises two (2) bending irons, the invention is not so limited insofar as one may use one bending iron and let the cage provide the other side of bending. Moreover, although in a preferred system comprising two (2) bending irons, each of the two (2) bending irons can have the ability to slide sideways in the bending cage, the invention is not so limited. One of the two bending bars could simply be placed in a separate slot without the ability to slide sideways and thereby be fixed in relationship to the bending cage. However the second bending bar would still operate as described and thereby allowing for the same functionality.

From the above, it can be understood that the present invention can provide one or more of the following advantages over the bending systems of the prior art:
1. The present invention can provide a means for controlling and imparting an applied direction of a bending force to a plate along a single axis of rotation;
2. The present invention can provide a means for preventing two bending tools from twisting away from an orientation of applied loads between the two tools that is along parallel planes and in opposite directions;
3. The present invention can provide a means that is simple, relatively inexpensive to manufacture, and of a small size and low weight that can reasonably be included in a tray for implants or other instruments, and is not bulky to package or store, or heavy or complicated to use; and 4. The present invention can provide a means that is simple to use and provides a user with the ability to contour a plate along any axis for the purpose of shaping a plate to more optimally fit a complex bone surface.

5. The present invention provides flexibility insofar as the bending bars and bending cage are not attached to each other whereby the bending bars can be used either separately from or in combination with the bending cage without the need to attach and reattach one to the other.

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. Thus, the present invention should not be limited by any of the above-described exemplary embodiments, but should be defined only in accordance with the following claims and their equivalents.

The invention claimed is:

1. A system for bending a plate or rod, comprising
(a) at least a first elongate bending bar comprising first and second ends and a body portion between the first and second ends, the at least first elongate bending bar having a longitudinal axis, the body portion comprising an upper surface and a lower surface defining a thickness t, the first end comprising an aperture or slot for engaging the plate or rod such that, with the plate or rod engaged in the aperture or slot, a bending force can be applied to the plate or rod by application of force to the second end of the at least first elongate bending bar; and
(b) a bending cage comprising a hollow interior and opposed front and rear surfaces separated by a distance d, each of the opposed front and rear surfaces defining an elongate opening formed with respective upper and lower parallel edges, each of the respective openings having a primary axis along a length thereof, respective dimensions of the respective openings, the distance d and the at least first elongate bending bar being such that (i) the at least first elongate bending bar is insertable through one of the respective openings in the front or rear surface to an operable position wherein the body portion of the at least first elongate bending bar is disposed within the bending cage with the first and second ends of the at least first elongate bending bar disposed outside of the bending cage at opposing sides of the bending cage, and (ii) with the at least first elongate bending bar in said operable position, the respective upper and lower parallel edges of the openings are disposed with respect to the upper and lower surfaces of the at least first elongate bending bar so as to permit lateral movement of the at least first elongate bending bar in a direction parallel to the primary axes of the respective openings but to restrict rotational movement of the bending bar about an axis substantially parallel to the longitudinal axis of the bending bar whereby, with the at least first elongate bending bar in the operable position in the bending cage and the plate or rod engaged in the aperture or slot in the first end of the at least first elongate bending bar, the bending cage restricts transfer of bending forces applied to the plate or rod by application of force to the second end of the at least first elongate bending bar to an axis that is parallel to the primary axes of the respective openings.

2. The system according to claim 1, wherein the respective elongate openings in the front and rear surfaces of the bending cage are of the same size.

3. The system according to claim 1, wherein a difference between the upper and lower edges of the opening in the front surface of the bending cage is slightly smaller than the thickness t of the at least first elongate bending bar.

4. The system according to claim 1, wherein a distance between the upper and lower edges of the respective openings in the front and rear surfaces is between about 0.5 and 4 cm.

5. The system according to claim 4, wherein the thickness t of the at least first elongate bending bar is between 0.5 and 4 cm.

6. The system according to claim 1, wherein the distance between the rear surface and front surface of the bending cage is about 2 to 10 cm.

7. The system according to claim 1, wherein the elongate opening in each of the front surface and rear surface of the bending cage is between about 4 and 22 cm in length.

8. The system according to claim 7, wherein the bottom, the top or both comprise an opening therein.

9. The system according to claim 1, wherein a length of the at least first elongate bending bar is between 10 and 50 cm.

10. The system according to claim 1, wherein the bending cage is of rectangular shape with, in addition to the front and rear surfaces, side walls, a bottom and a top.

11. A system for bending a plate or rod, comprising
(a) at least first and second elongate bending bars each comprising first and second ends and a body portion between the first and second ends, each of the at least first and second bending bars having a longitudinal axis, the body portion of each of the at least first and second bending bars comprising an upper surface and a lower surface defining a thickness t, the first end of each of the at least first and second bending bars comprising an aperture or slot for engaging the plate or rod such that, with the plate or rod engaged in the apertures or slots of the respective at least first and second bending bars, a bending force can be applied to the plate or rod by application of force to the second ends of the respective bending bars; and
(b) a bending cage comprising a hollow interior and opposed front and rear surfaces separated by a distance d, each of the opposed front and rear surfaces defining an elongate opening formed with respective upper and lower parallel edges, each of the elongate openings having a primary axis along a length thereof, respective dimensions of the elongate openings, the distance d and the at least first and second bending bars being such that (i) the at least first and second bending bars are insertable through one of the respective openings in the front or rear surface to an operable position wherein the respective body portions of the at least first and second bending bars are disposed within the bending cage with the respective first and second ends of the at least first and second bending bars disposed outside of the bending cage at opposing sides of the bending cage, and (ii) with the at least first and second bending bars in said operable position, the respective upper and lower parallel edges of the openings are disposed with respect to the respective upper and lower surfaces of the at least first and second bending bars so as freely to permit lateral movement of the at least first and second bending bars in a direction parallel to the primary axes of the respective openings but to restrict rotational movement of the at least first and second bending bars about an axis substantially parallel to the respective longitudinal axes of the at least first and second bending bars whereby, with the at least first and second bending bars in the operable position in the bending cage and the plate or rod engaged in the apertures or slots in the respective first ends of the at least first and second bending bars, the bending cage restricts transfer of bending forces applied to the plate or rod by application of force to the respective second ends of the at least first and second bending bars to an axis that is parallel to the primary axes of the respective openings.

12. The system according to claim 11, wherein respective lengths of the elongate openings of the at least first and second bending bars are such that, with the at least first and second bending bars in the operable position, with the plate or rod engaged in the respective apertures or slots of the respective first ends of the at least first and second bending bars and with the respective first ends of the at least first and second bending bars adjacent to each other, the at least first and second bending bars can be moved in the direction parallel to the respective primary axes of the respective elongate openings a distance sufficient to increase an angle between the at least first and second bending bars from 0° to 45°.

13. The system according to claim 11, wherein a distance between the upper and lower edges of the opening in the front surface of the bending cage is slightly smaller than the thickness t of the at least first elongate bending bar.

14. The system according to claim 11, wherein a distance between the upper and lower edges of the opening in each of the front and rear surfaces is between about 0.5 and 4 cm.

15. The system according to claim 14, wherein the thickness t of each of the at least first and second bending bars is between 0.5 and 4 cm.

16. The system according to claim 11, wherein the distance between the rear surface and front surface of the bending cage is about 2 to 10 cm.

17. The system according to claim 11, wherein the elongate opening in each of the front surface and rear surface of the bending cage is between about 4 and 22 cm in length.

18. A method for bending a plate or rod sideways in a plane of the plate or rod, the method comprising:
(a) providing the system of claim 11;
(b) inserting the at least first and second bending bars through the respective elongate openings in the front and rear surfaces of the bending cage;
(c) inserting the plate or rod in the respective apertures or slots at the respective first ends of the at least first and second bending bars; and
(d) applying force to the respective second ends of the at least first and second bending bars to move the respective second ends of the at least first and second bending bars apart or further apart whereby to impart a bending force on the plate or rod in the plane of the plate or rod.

19. A method for bending a plate or rod sideways in a plane of the plate or rod, the method comprising:
(a) providing the system of claim 12;
(b) inserting the at least first and second bending bars through the respective elongate openings in the front and rear surfaces of the bending cage;
(c) inserting the plate or rod in the respective apertures or slots at the respective first ends of the at least first and second bending bars; and
(d) applying force to the respective second ends of the at least first and second bend bars to move the respective second ends of the at least first and second bending bars apart or further apart whereby to impart a bending force on the plate or rod in the plane of the plate or rod.

20. A system for bending an implant in a single plane, said system comprising
(a) at least a first elongate bending bar having a first end, a second end, and a body disposed between the two, said first end having at least one of an aperture or slot for engaging the outer surface of at least a portion of said implant at a point of contact;
(b) a bending cage comprising at least one of an aperture or slot for allowing insertion of said at least first elongate bending bar into the bending cage, and means for (i) allowing the at least first elongate bending bar inserted into the bending cage movement along a single plane while constraining translational movement and rotation of the at least first elongate banding bar out of said plane, and (ii) engaging said at least first elongate bending bar at a site of contact such that distraction of said second end of the first elongate bending bar in relation to said bending cage results in creation of a torque to bend said implant around an axis that is located adjacent to the point of contact of said first end of the at least first elongate bending bar with said implant.

* * * * *